United States Patent [19]

Bucalo

[11] 4,279,256

[45] Jul. 21, 1981

[54] NERVE STIMULATION METHOD

[76] Inventor: Louis Bucalo, 155 Roberts St., Holbrook, N.Y. 11741

[21] Appl. No.: 31,982

[22] Filed: Apr. 20, 1979

Related U.S. Application Data

[60] Continuation of Ser. No. 756,970, Jan. 5, 1977, abandoned, which is a division of Ser. No. 513,295, Oct. 9, 1974, Pat. No. 4,005,699.

[51] Int. Cl.³ .............................................. A61N 1/36
[52] U.S. Cl. ................................ 128/419 R; 128/784
[58] Field of Search ............... 128/386, 419 R, 8, 421, 128/422, 423, 784, 788, 794, 802

[56] References Cited

U.S. PATENT DOCUMENTS

| | | | |
|---|---|---|---|
| 926,384 | 6/1909 | Boyd | 128/794 |
| 2,764,683 | 9/1956 | Paust et al. | 128/423 |
| 3,403,684 | 10/1968 | Stiebel et al. | 128/788 |

*Primary Examiner*—William E. Kamm
*Attorney, Agent, or Firm*—Steinberg & Raskin

[57] ABSTRACT

Methods and devices for purposes such as nerve stimulation and sexual stimulation. For purposes of nerve stimulation, a plurality of electrically conductive bodies are suspended in a viscous substance and injected into tissue so as to extend between the outer skin and a nerve, for providing an electrical path from the outer skin to the nerve in order to stimulate the latter. For purposes of sexual stimulation, an energy pulse train is applied with an amplitude envelope varying cyclically in a manner corresponding to pelvic thrusting during sexual intercourse.

2 Claims, 13 Drawing Figures

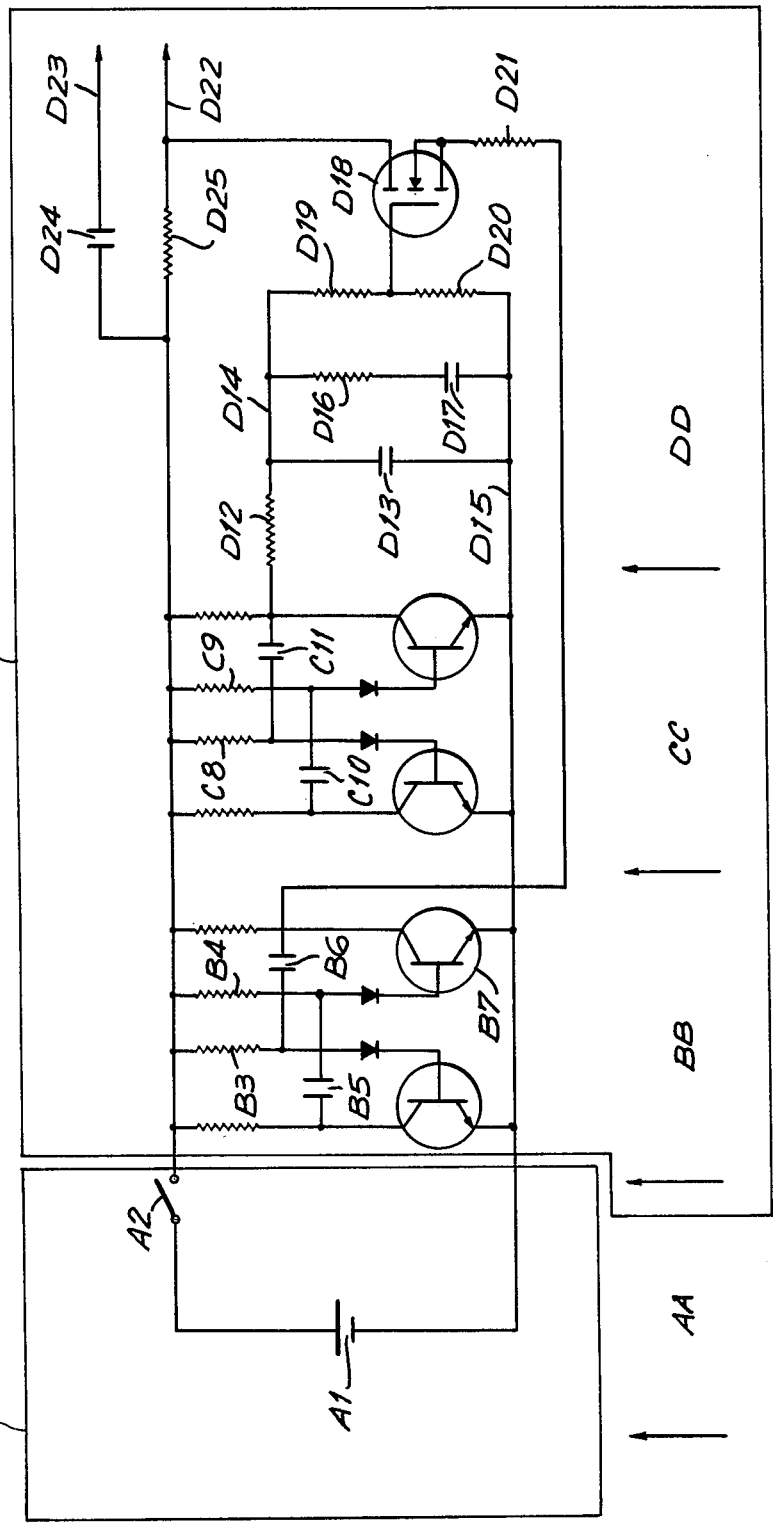

4,279,256

NERVE STIMULATION METHOD

CROSS REFERENCE TO RELATED APPLICATION

This is a continuation of application Ser. No. 756,970, filed Jan. 5, 1977, now abandoned which is a division of copending application Ser. No. 513,295, filed Oct. 9, 1974, now U.S. Pat. No. 4,005,699.

BACKGROUND OF THE INVENTION

The present invention relates to methods, to be used in providing for living beings treatments such as rendering a stimulation path electrically conductive, or achieving direct nerve stimulation for a body function such as sexual stimulation.

As is well known, many male individuals suffer from an incapability of achieving satisfactory sexual intercourse, primarily because of any inability to achieve and maintain a satisfactory penile erection. In general, it is known that for many different purposes it is desirable to conduct electrical energy from an external source to a part of a living being such as a nerve, for example, but up to the present time efficient transmission of electrical energy for this purpose has been unsatisfactory because of the fact that the electrical energy becomes dissipated in the tissue before reaching the desired location unless conductors are implanted surgically with the associated trauma and damage.

In connection with conducting electricity without surgery to an interior body part such as a nerve, for example, at the present time an estimate is made of the best location for an electrode to be placed in engagement with the exterior of the body, and then electrical energy is transmitted by way of the electrode but becomes rapidly dissipated to a large extent in the body tissue before reaching the desired location.

In addition, in connection with rigid penile implants, while various procedures and devices have been used particularly in connection with stimulating penile erection, up to the present time all of the known procedures have proved to be less than satisfactory because of radical alteration of natural conditions.

SUMMARY OF THE INVENTION

It is accordingly a primary object of the present invention to provide methods, for avoiding the above drawbacks.

In addition, it is an object of the present invention to provide methods suitable for efficiently conducting electricity to a predetermined part such as a nerve without the use of damaging surgical procedures.

Furthermore, it is an object of the present invention to provide methods for effectively achieving penile erection and artificially assisted sexual intercourse.

In accordance with the invention, for purposes such as nerve stimulation, there is introduced into the tissue a viscous substance which has a plurality of electrically conductive bodies suspended therein and distributed therethrough, these electrically conductive bodies being capable of conducting electricity efficiently through the tissue of a living being to a location such as a nerve which may be stimulated in connection with sexual stimulation.

Also, for the purpose of sexual stimulation, an electrode may be placed in engagement with the penis, preferably at the rear thereof just behind the glans, and this electrode is situated in an electrical circuit which provides through the electrode electrical energy first to an extent sufficient to create an erection, then to a lesser extent sufficient to maintain the erection or cyclically at a frequency corresponding to the frequency of normal pelvic thrusting during sexual intercourse. According to a particular feature of the invention, the supply of the electrical energy is controlled primarily by regulating the peak value of a short duration current pulse.

BRIEF DESCRIPTION OF THE DRAWINGS

The invention is illustrated by way of example in the accompanying drawings which form part of this application and in which:

FIG. 8B is a schematic wiring diagram of the device to produce stimulation and excitation of body functions in the manner shown in FIG. 6B.

DESCRIPTION OF PREFERRED EMBODIMENTS

Figure 1:
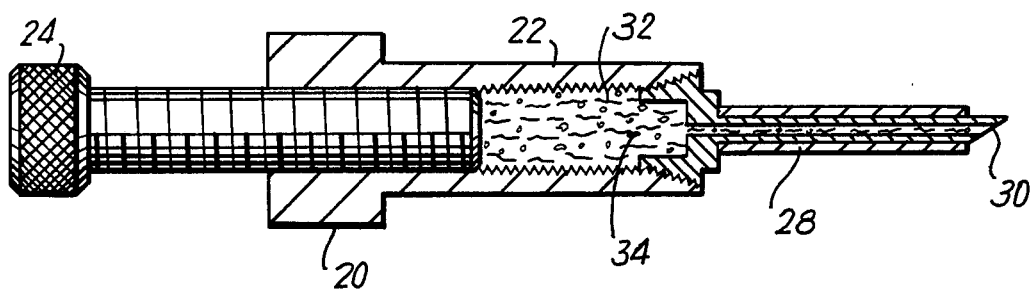
FIG. 1 is a fragmentary partly sectional schematic illustration of a syringe containing materials according to the invention which are introduced into tissue according to the method of the invention.

In connection with providing a conductive path in the body of a living being, the method of the invention involves introducing into the tissue a viscous substance in which electrically conductive bodies are suspended while being distributed throughout the substance. The introduction of the substance with the bodies suspended therein is carried out, for example, by way of a screw type syringe 20 as schematically shown in FIG. 1. Thus, the syringe 20 has a hollow barrel 22 which receives the screw plunger 24. The outlet of the barrel 26 is connected to the needle 28 the tip 30 of which is introduced into the tissue at the part thereof which is to receive the materials (32 and 34) of the invention. These materials are shown in the barrel 22 in FIG. 1. Thus FIG. 1 shows a viscous substance 32 having the bodies 34 suspended therein and distributed therethrough.

In the preferred embodiment of the invention, the substance 32 is to be absorbed by the body and it may take the form of a vegetable oil or gelatin. The bodies 34 are preferably particles, but may include some elongated fibers as illustrated schematically in FIG. 1. Sufficient bodies 34 are suspended in the substance 32 so as to be distributed completely therethrough with the bodies 34 randomly engaging each other. The bodies 34 are made of materials which will be compatible with the body. Thus they may take the form of particles or fibers of gold, platinum, magnetic materials such as a platinum-cobalt alloy, gold plated magnetic materials, or the like, and it is also possible to use suitable absorbable materials or plastic materials for the bodies 34 combined with x-ray opaque materials.

According to a particular feature of the invention it is preferred to use for the substance 32 viscous hydrogenated vegetable oil, because in this case the time of absorption of the viscous substance may be controlled by the degree of hydrogenation, so that after the viscous substance 32 has been absorbed and replaced by tissue there remains in the living being a tissue portion composed of natural body tissue which itself has grown into the spaces between the bodies 34.

As has been indicated above, it is desirable under some circumstances to transmit electrical energy to certain parts of the body. For example it is well known that certain therapeutic procedures require transmission of electrical energy to a nerve. At the present time in order to carry out procedures of this latter type an approximation is made of the location of the exterior surface of a living being which is closest to the nerve or the like to which electrical energy is to be transmitted, and then an electrode is placed in engagement with the skin at the estimated location for transmitting electrical energy through the tissue to the nerve or the like. However, the result is that a considerable amount of the electrical energy is undesirably and inefficiently dissipated through the body tissue before reaching the desired location such as a nerve or the like. Alternatively, wires are implanted surgically in order to improve procedures of this type.

Figure 2:
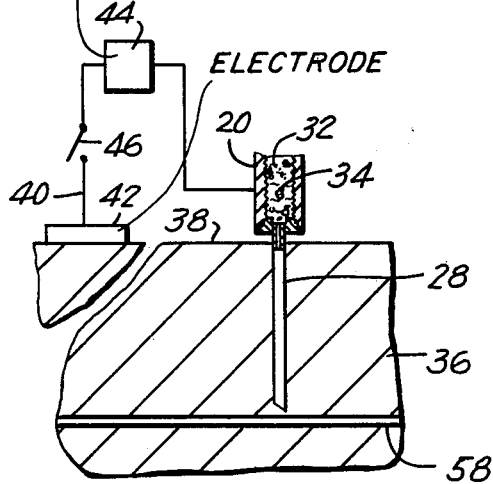
FIG. 2 is a schematic illustration of part of a method of the invention used in connection with rendering a tissue pathway electrically conductive.
Figure 3:
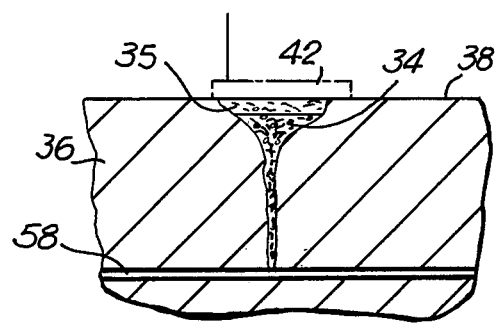
FIG. 3 is a schematic illustration of materials situated in tissue for rendering a pathway in the latter electrically conductive.

The present invention provides the method and materials illustrated schematically in FIGS. 2 and 3. Thus, FIGS. 2 and 3 show fragmentarily in a schematic manner tissue 36 situated beneath the skin 38 which is at the exterior of the body, this tissue 36 having embedded therein a nerve 58.

According to the invention, the syringe 20 has a metallic needle 28, which is electrically conductive internally and preferably insulated externally. For the purposes shown in FIGS. 2 and 3, the substance 32 may be hydrogenated vegetable oil while the bodies 34 are in the form of elongated electrically conductive particles, made of any conductor such as gold or platinum, these bodies being suspended in the substance 32 in a concentration sufficient to assure that the bodies are distributed throughout the substance 32 and engage each other. It is most preferable, however, to use magnetic bodies 34. With the syringe 20 thus provided with a quantity of the substance 32 with the bodies 34 suspended therein, the needle 28 is introduced into the tissue 36, hopefully in a proper position for engaging the nerve 58, as shown in FIG. 2. In order to check the location of the needle 28, it is located in an electrical circuit 40 having an electrode 42 placed in engagement with the skin 38 as well as a source of electrical stimulation 44 and a switch 46. First the switch 46 is closed so as to complete the circuit, and apply the stimulus and the physician will check as to whether the desired effect is achieved. If the desired effect is not achieved, the physician knows that the needle 28 has not been properly located and will remove the needle and relocate it. When the desired effect is achieved upon closing the switch 46, the physician knows that the needle 28 has been properly situated, and then the needle 28 is withdrawn while the plunger 24 is turned into the barrel 22 so as to leave in the tissue 36 a quantity of the substance 32, as shown schematically in FIG. 3, having the electrically conductive bodies 34 distributed therethrough. As was indicated above, it is preferred to use for the substance 32 an absorbable medium which will be replaced by tissue 36 which grows into the spaces between and engages the bodies 34. Also, by using magnetic bodies 34 (e.g. any magnetic materials covered with gold or compatible magnetic materials such as a platinum-cobalt alloy), they can be converted into permanent magnets after injection, by placing a suitable strong magnet adjacent the injection, and then the magnetized particles attract and press against each other to provide a highly effective electrically conductive path of low resistance. With the living being treated in the manner shown in FIG. 3, the physician can always locate by x-ray where the bodies 34 are located in the tissue 36, or, if preferred, a suitable permanent mark may be made at the skin 38 to indicate the location of the bodies 34. Thereafter whenever it is desired to transmit electrical energy to this predetermined part of the body, such as the nerve 58, an electrode 42 attached to a stimulator is placed in engagement with the skin 38 in line with the bodies 34 so that the electrical energy is transmitted directly through the bodies 34 to the nerve 58 without undesirable, inefficient dissipation of the electrical energy through the tissue 37. A combination of electrically conductive bodies injected towards a nerve and magnetic particles 35 injected below and near the skin is very effective for maintaining good electrode contact. Typically, electrodes are held in place over the skin with adhesive tapes in combination with electrode jelly. In practice, the adhesive tape does not provide a normal force perpendicular to the skin and the electrical impedance of the contact varies appreciably particularly with muscular motion. Often the electrode jelly migrates and renders the adhesive ineffective. Thus in FIG. 3, the region of the injected materials 35 may be magnetic particles and the electrode 42 may be a conductive permanent magnet which requires no further electrode attachment means.

Figure 4A:
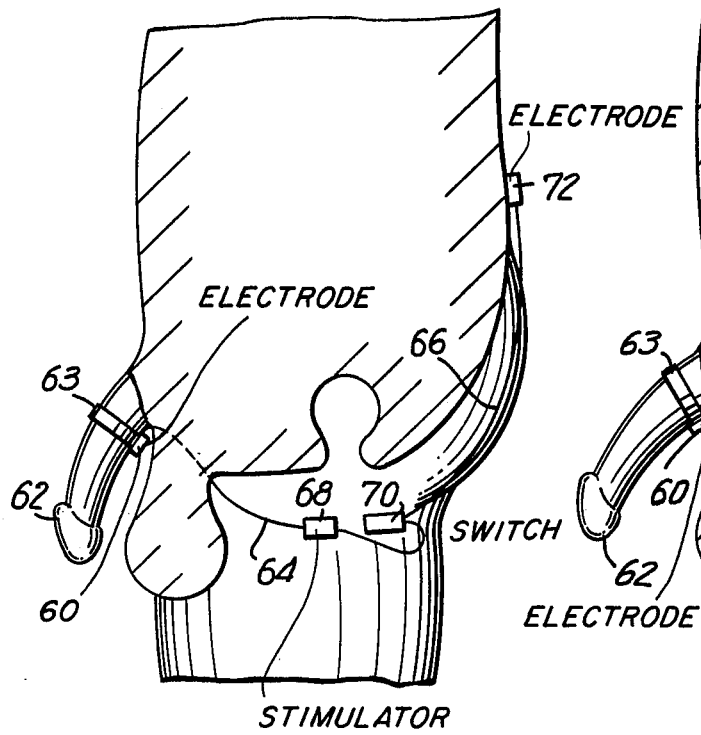
FIG. 4A is a schematic illustration of a method and device of the invention for achieving penile erection and sexual stimulation.
Figure 4B:
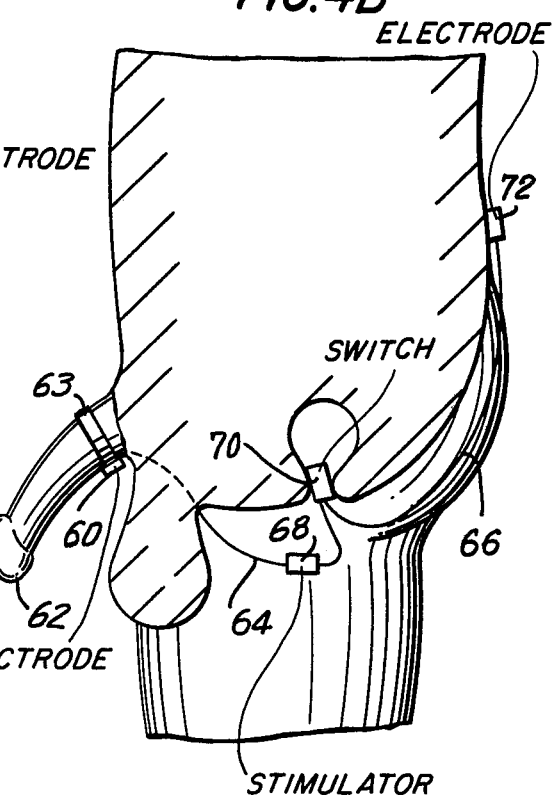
FIG. 4B is a schematic illustration with anal control of the stimulus.

FIGS. 4A and 4B illustrate methods and devices of the invention to be used in connection with achieving and maintaining a satisfactory penile erection as well as achieving satisfactory sexual intercourse. Referring to FIG. 4A it will be seen that an electrode 60 is placed in engagement with the penis 62. The electrode 60 is shown in FIG. 4A at a scale, with respect to the penis, which is larger than the actual electrode. In practice, the electrode 60 is small enough to be attached to the penis 62 without creating any discomfort during sexual intercourse. Although the electrode 60 can be placed in engagement with any part of the penis, it has been found from experimentation that outstanding results are achieved by situating the electrode 60 at the location shown in FIG. 4A. Thus the electrode 60 is situated, in accordance with the invention, at the rear of the penile shaft behind the glans 62. The electrode 60 may be maintained at the illustrated location in any suitable way as by application of a suitable strip of adhesive tape 63. If desired, a condom may be placed around the penis with the electrode 60 being situated within the condom at the location illustrated to be retained in the illustrated position by the elastic condom. Since under these conditions the condom need not be used for preventing conception or for preventing venereal disease, the closed end of the condom may be removed to expose the glans 62, thus leaving in effect an elastic sleeve which reliably maintains the electrode 60 in the desired location.

An elongated electrical conductor 64, suitably insulated at its exterior, is electrically connected with and extends from the electrode 60 in the manner illustrated in FIG. 4A. This conductor 64 also is made of a wire fine enough to prevent any discomfort during coitus. The conductor 64 is electrically connected with a stimulator 68 which is connected by conductor 64' to switch means 70 the details of which are described below in connection with FIGS. 6A, 6B, 6C, 7, 8A, 8B and 9. The switch means 70 is of a size and configuration enabling it to be placed in the anal canal, as illustrated schematically in FIG. 4B, thus enabling the switch 70 to be opened and closed by the anal sphincter. As will be apparent from the description below in connection with FIG. 9, contraction of the anal sphincter will close the switch while relaxing the sphincter will open the switch. A further conductor 66 extends from the stimulator and switch means to a second electrode 72 which completes the circuit throughout the body.

Figure 7:
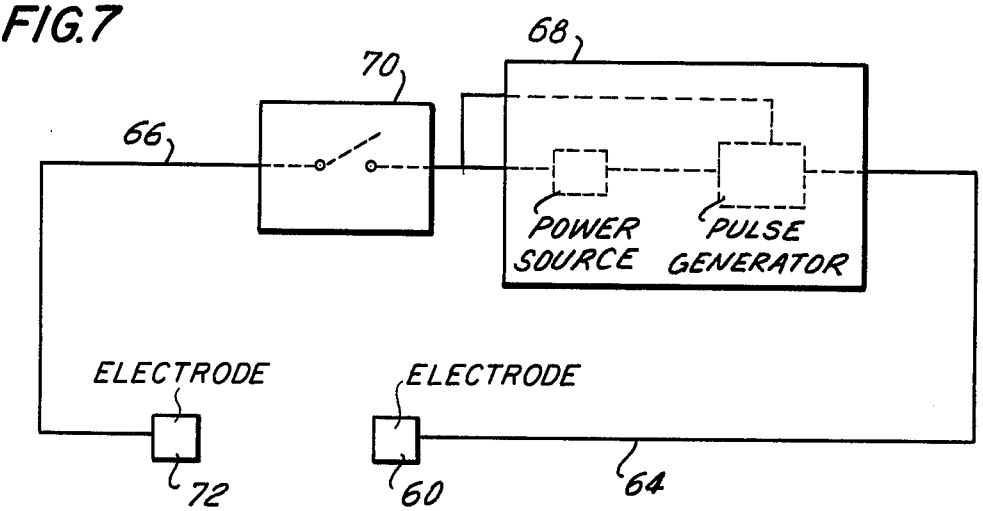
FIG. 7 is a schematic wiring diagram of the device to produce stimulation and excitation of body functions as shown in FIGS. 4A and 4B.

As indicated in FIG. 7, the stimulator 68 contains components such as power source, and pulse generator.

Figure 6A:
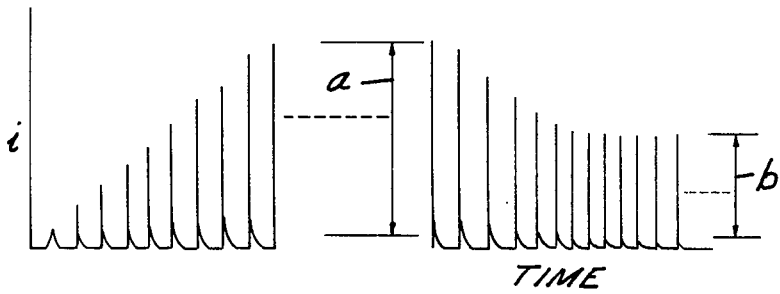
FIGS. 6A, 6B and 6C are graphs illustrating the manner in which electrical energy is supplied.
Figure 8A:
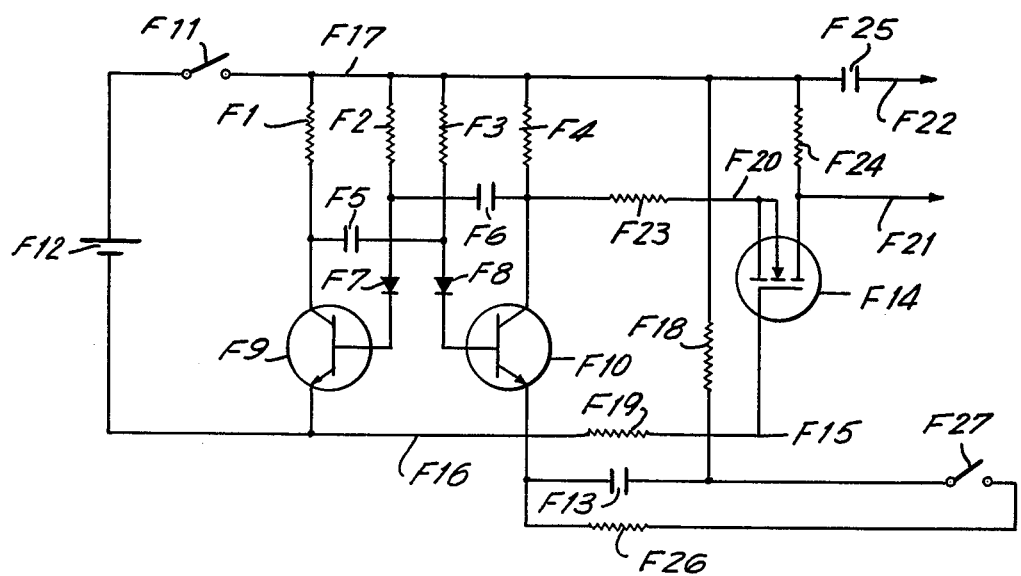
FIG. 8A is a schematic wiring diagram of the device to produce stimulation and excitation of body functions in the manner shown in FIG. 6A with switch control of the stimulus magnitude.

Referring to FIG. 6A it will be seen that by way of the electrical circuit means shown in FIG. 8A there is first provided electrical energy to the extent a, shown in FIG. 6A, which may be on the order of 2 milliamps, for example, and this extent of electrical energy is often sufficient for achieving an erection with the electrode 60 located as illustrated in FIG. 4A and electrode 72 engaging any other part of the body for completing the circuit through the body. Thereafter, through a suitable control in the stimulator the extent to which electrical energy is supplied is reduced to the lesser extent b, indicated in FIG. 6A, which may be on the order of 0.5 milliamps, for example. It has been shown to be possible in this way, with this lesser supply of electrical energy, to maintain the erection initially achieved by the larger supply of electrical energy.

One of many possible circuits for generating the desired controllable stimulus is shown in FIG. 8A. Resistors F1, F2, F3 and F4; capacitors F5 and F6; diodes F7 and F8; and transistors F9 and F10 form an astable multivibrator of standard design. When on-off switch F11 is closed, the multivibrator is energized by battery F12 and commences oscillation. The time constants of resistor F2 with capacitor F6 and of resistor F3 with capacitor F5 are chosen such that the multivibrator generates on the order of 200 pulses per second, with transistor F10 in saturated conduction for approximately 200 microseconds of each cycle.

As there is no charge on capacitor F13 immediately after closure of switch F11, enhancement mode field effect transistor F14 initially does not conduct during any part of the multivibrator cycle. With the passage of time, however, the potential on conductor F15 builds asymtotically toward a value part way between the potentials of conductors F16 and F17, as determined by the relative values of resistors F18 and F19. By the source follower action of transistor F14 the potential on conductor F20 is prevented from falling below that on conductor F15 by more than the threshold voltage of this transistor, provided that the impedance presented by the individual to output conductors F21 and F22 is not excessively high. Thus during the conduction periods of transistor F10, a current pulse proportional in magnitude to the potential on conductor F15 and to the conductance of resistor F23 is drawn through the individual. During the periods when transistor F10 is in the off state a small reverse current flows through the individual and resistor F24, caused by charge on capacitor F25. In steady-state operation, this capacitor loses as much charge through this reverse flow as it gains through forward pulse flow. Therefore, there is no undesirable D.C. component in the current flow through the body of the individual. Since the output of the device consists of a train of pulses determined in current rather than in voltage, the strength of stimulation is made independent of variations in body impedance of the individual.

Resistor F26 and switch F27 provide the person with a means of controlling the strength of stimulation beyond more on-off control. Closure of switch F27 causes the potential on conductor F15 to fall toward a lower value, thereby lowering the level of stimulation. If switch F27 is opened again, the stimulus again builds slowly to its maximum value.

The output of this device is shown in FIG. 6A. For clarity, the great majority of individual pulses have been omitted.

Figure 6C:
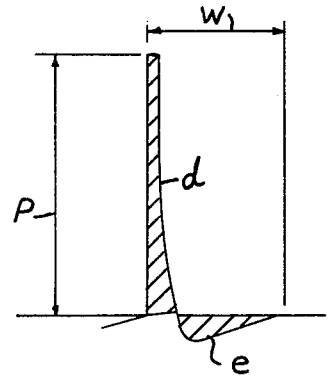
Figure 6B:
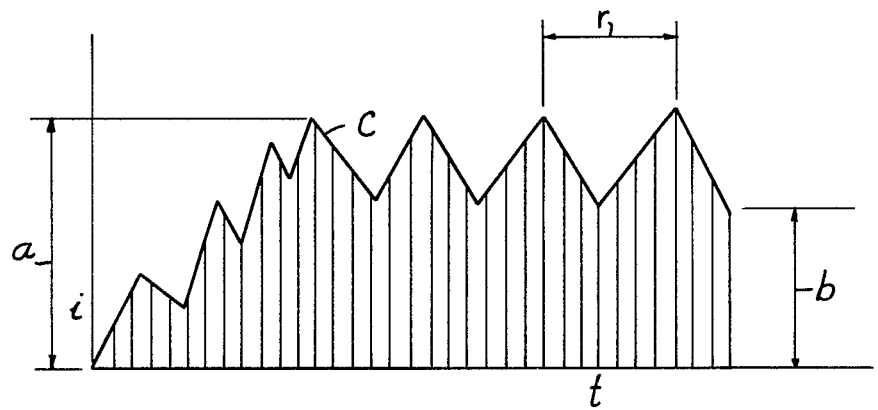

Alternatively, in accordance with a particular feature of the invention, the stimulator 68 operates automatically to provide a cyclical supply of energy as indicated in FIG. 6B. The controls are such that the cycles r have a frequency on the order of 75 cycles per minute, closely corresponding to the frequency of pelvic thrusting during normal sexual intercourse. It has been found from experimentation, that the cyclical envelope of stimulation shown in FIG. 6B, corresponding to a normal frequency of pelvic thrusting, is extremely effective for reliably maintaining the penis in an erect condition. FIG. 8B shows one of many possible circuits to produce the stimulus of FIG. 6B. For purposes of description, the circuit is divided into four sections.

Section AA is the energizing means, consisting of battery A1 and on-off switch A2.

Sections BB and CC are astable multivibrators of standard design. The values of resistors B3 and B4 and of capacitors B5 and B6 are chosen such that multivibrator BB generates highly asymmetrical pulses at a rate of roughly 200 per second, with transistor B7 in saturated conduction for about 200 microseconds of each cycle. The values of resistors C8 and C9 and of capacitors C10 and C11 are chosen such that multivibrator CC generates either symmetrical pulses or moderately asymmetrical pulses, as is found most advantageous. The repetition rate of multivibrator CC is about 1 per second.

Signals from the two multivibrators are combined in section DD to produce the desired output. During the conduction periods of transistor B7, field effect transistor D18 acts as a constant current sink from output conductor D22. Thus pulses of current pass from the positive side of the battery A1, through the output capacitor D24, through output conductor D23, through the body of the individual, back through output conductor D22, through transistor D18, through resistor D21, through transistor B7 and thence back to the battery. During the periods when transistor B7 is in the off state a small reverse current flows through the body and resistor D25 caused by residual charge on capacitor D24. In steady-state operation, this capacitor loses as much charge through this reverse flow as it gains through forward pulse flow. Therefore, there is no undesirable D.C. component in the current flow through the individual's body. Since the output of the device consists of a train of pulses determined in current rather than in voltage, the strength of stimulation is made independent of variations in body impedance.

The amplitude of the circuit's output depends directly upon the gate voltage of transistor D18, and this fact is exploited to provide modulation of the stimulus strength. The most advantageous modulation must have two features: a slow initial build-up of strength, and a cyclically repeating variation of strength having a period of about 1 second. A modulating signal providing these features is derived from the output of multivibrator CC by the filtering action of components D12, D13, D16, and D17. Since the time constant of resistor D12 and capacitor D13 is chosen to be longer than the period of multivibrator CC, a roughly triangular voltage waveform appears on conductor D14. While the zero initial charge on capacitor D13 prevents the build up of stimulus from occurring very rapidly when switch A2 is closed, provision of resistors D19 and D20 allows their build up to be further slowed. By proper choice of components D12, D13, D16, and D17, a wide range of different depths of modulation and rates of build up can be achieved. While with appropriate choice of resistor D21 the potential of conductor D14 could be applied directly to the gate of transistor D18, inclusion of the divider consisting of resistors D19 and D20 allows the device to operate off a lower voltage batter.

The output current waveform of the device is shown in FIG. 6B. For clarity, the great majority of the individual pulses have been omitted. A typical pulse is shown in FIG. 6C wherein the areas d and e cancel each other to give a zero net flow of charge in each cycle.

Figure 5:
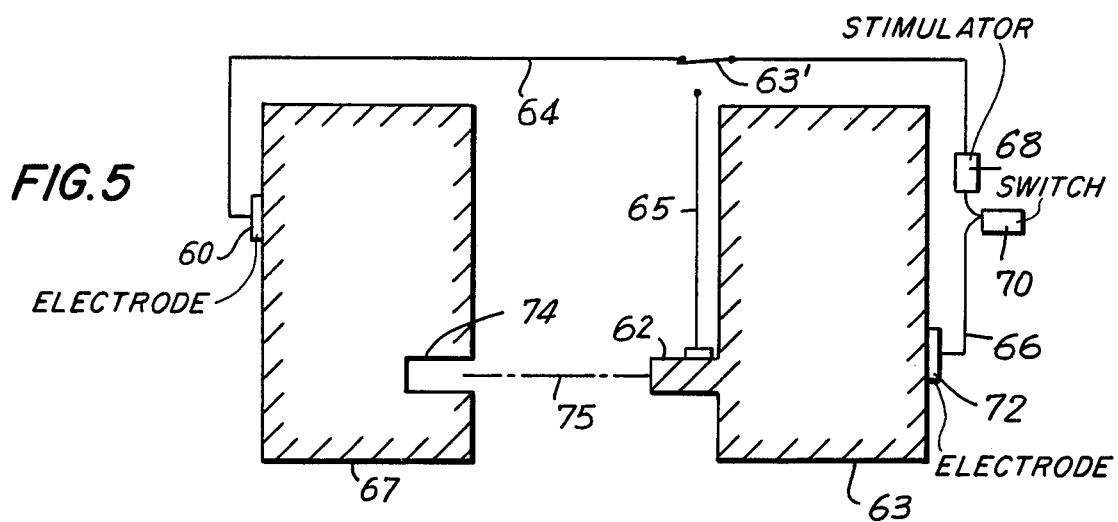
FIG. 5 is a schematic illustration of possible manners in which the device of FIG. 4A or 4B may be used, according to a further feature of the invention.

Although, as has been indicated above, the electrode 72 can be placed in engagement with any part of the male, it is possible, according to a further feature of the invention, to provide an arrangement as shown in FIG. 5 where the conductor 64 has a length sufficient to enable the electrode 60 to complete the circuit through the penis by being placed in engagement with the body of the female partner. Thus as is schematically illustrated in FIG. 5, the electrode 60 may be placed, for example, in engagement with the back of the female partner held thereon in any suitable way as by suitable tape, if desired, although it is also possible for the male participant to hold the electrode 60 in engagement with the female participant manually. With such an arrangement when the penis 62 is introduced to the vagina 74, schematically indicated in FIG. 5, the electrical circuit 75 will then be completed by the vagina 74 and the penis 62, for maintaining an effective sexual excitation and penile erection in a manner affording a highly satisfactory coital connection. It is also possible, however, to complete the circuit through the penis 62 instead of through the female partner by branching a conductor 65 from the conductor 64 and connecting the conductor 65 to an electrode held in engagement with the penis in a manner schematically shown in FIG. 5. At the junction between the conductors 64 and 65 there is a manually operable switch 63' which in one position disconnects the conductor 65 from the conductor 64 and completes a circuit through the portions of the conductor 64 which are interconnected by the switch 63', while in another position of switch 63' the conductor 65 is electrically connected only with that part of the conductor 64 which extends from the switch 63' to the control unit 68. Thus with this arrangement the male individual 63 has the option of completing the circuit held through the female partner or through his own body. The utilization of current controlled stimuli which follow schedules described in FIGS. 6A or 6B is more effective than continuous pulse train excitation for the methods and equipment to achieve sexual excitation as described in co-pending application Ser. No. 418,106 as well as the sexual stimulation methods and equipment shown schematically in FIGS. 4A, 4B and 5.

It has been found experimentally that because of changing impedances caused by electrode conditions or fatty tissue existing between the skin and the nerves that more reliable stimulation can be achieved by automatic regulation which controls the peak current value rather than a controlled voltage.

Figure 9:
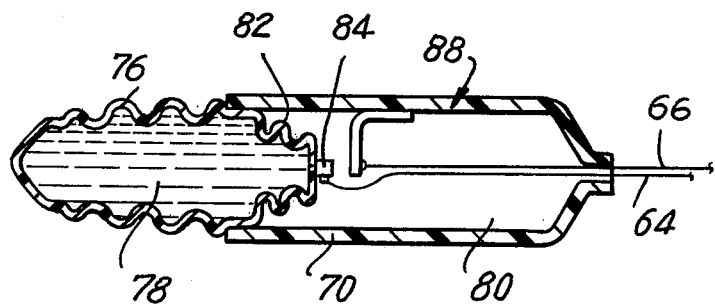
FIG. 9 is a sectional illustration of a structure for controlling a switch with the anal sphincter.

Inasmuch as during use of a stimulator device there may be an inconvenience involved in closing or opening the switch means 70, according to a further feature of the invention the switch means 70 has a construction to provide for anal spincter actuation, as shown, for example, in FIG. 9. Thus the switch means 70 includes an outer flexible enclosure 76 made of any suitable plastic which is not electrically conductive and which is impervious to a liquid 78 which may take the form of any suitable oil or the like situated in a space within the flexible enclosure 76 as illustrated in FIG. 9. The space 78 is closed off from the rest of the interior 80 of the enclosure 88 by a flexible wall 82. The wall 82, which is not electrically conductive, carries one contact 84 of the switch means 70, this contact 84 being connected, for example, to the conductor 64. The other conductor 66 is connected to a stationary contact 86 which is fixed to the inner surface of the enclosure 88 in the manner illustrated in FIG. 9. The closure 88 which carries part 76 which contains the liquid 78 is situated in the anal canal at a location for responding to contraction of the anal sphincter so that when the anal sphincter is contracted the wall 82 will bulge toward the stationary contact 86 placing the contact 84 in engagement with the contact 86 for closing the switch means 70. Of course when the sphincter is relaxed the switch will automatically open. Thus through this arrangement or other force actuated means known to those skilled in the art, the switch means 70 can readily be inserted into the anal canal for actuation by the anal sphincter in a highly convenient manner.

As has been indicated above in connection with FIG. 3, the conductivity of the body of particles 34 shown in FIG. 3 is increased very greatly by utilizing electrically conductive magnetic particles which attract each other so that as a result of the contact between these particles the resistance is lowered considerably.

What is claimed is:

1. In a method for stimulating a nerve, the steps of injecting into body tissue in a suitable carrier a plurality of electrically conductive particles extending from a nerve which is to be stimulated to the region of the outer skin to form a direct electrically conductive path from a point within the skin to a nerve to be stimulated, and thereafter when it is desired to stimulate the nerve situating an electrode at the skin in line with the electrically conductive particles, and transmitting electrical energy through said electrode and said electrically conductive particles to said nerve so as to stimulate the latter.

2. The method of claim 1 and wherein the injection of the carrier with electrically conductive particles is effected at a region such that the particles are in contact with a nerve in contact with the penis.

* * * * *